(12) United States Patent
Doshi et al.

(10) Patent No.: US 9,168,360 B2
(45) Date of Patent: *Oct. 27, 2015

(54) METHOD AND A BALLOON CATHETER ASSEMBLY FOR TREATING BIFURCATION LESIONS

(71) Applicant: Concept Medical, Inc., San Jose, CA (US)

(72) Inventors: Manish Doshi, Surat (Gujarat) (IN); Divyesh Sherdiwala, Surat (Gujarat) (IN); Prakash Sojitra, Surat (Gujarat) (IN)

(73) Assignee: CONCEPT MEDICAL RESEARCH PRIVATE LIMITED, Surat (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/083,422

(22) Filed: Nov. 18, 2013

(65) Prior Publication Data

US 2014/0142503 A1 May 22, 2014

Related U.S. Application Data

(63) Continuation-in-part of application No. 13/124,119, filed as application No. PCT/IN2011/000032 on Jan. 17, 2011, now Pat. No. 8,585,642, and a continuation-in-part of application No. 12/920,812, filed as application No. PCT/IN2010/000349 on May 21, 2010.

(30) Foreign Application Priority Data

Jun. 2, 2009 (IN) .......................... 1337MUM2009
Jan. 22, 2010 (IN) ............................ 176MUM2010

(51) Int. Cl.
| | |
|---|---|
| *A61M 29/00* | (2006.01) |
| *A61M 25/10* | (2013.01) |
| *A61L 29/08* | (2006.01) |
| *A61L 29/16* | (2006.01) |
| *A61K 9/127* | (2006.01) |

(52) U.S. Cl.
CPC ............ *A61M 25/1011* (2013.01); *A61K 9/127* (2013.01); *A61L 29/085* (2013.01); *A61L 29/16* (2013.01); *A61L 2300/624* (2013.01); *A61L 2400/12* (2013.01); *A61M 25/1002* (2013.01); *A61M 2025/105* (2013.01); *A61M 2025/1045* (2013.01); *A61M 2025/1088* (2013.01)

(58) Field of Classification Search
CPC .................... A61L 2300/624; A61L 2400/12; A61L 29/085; A61L 29/16; A61M 2025/105; A61M 2025/1088; A61M 25/1011; A61M 2025/1045; A61M 25/0045; A61M 25/10; A61M 25/1027; A61K 9/127
USPC ..................................................... 604/101.04
See application file for complete search history.

(56) References Cited

U.S. PATENT DOCUMENTS

5,669,924 A * 9/1997 Shaknovich .................. 623/1.11
2005/0129727 A1* 6/2005 Weber et al. .................. 424/423

*Primary Examiner* — Jason Flick
(74) *Attorney, Agent, or Firm* — Timberline Patent Law Group PLLC (57) ABSTRACT

A balloon catheter assembly for delivering nano-carriers to bifurcation lesions in one or more of a main branch and a side branch of a blood vessel bifurcation within 30 to 90 seconds is provided. The balloon catheter assembly includes two or more balloons designed for use in the blood vessel bifurcation. The balloon catheter assembly may also include one or more stents. A surface of one or more of the two or more balloons is coated with the nano-carriers. Stents, when included, may also be coated with the nano-carriers. The nano-carriers include one or more drugs encapsulated with one or more biological agents.

12 Claims, 10 Drawing Sheets

| Process | CV Number | Timepoint | Animal Number | Vessel/Stent Type | |
|---|---|---|---|---|---|
| | | | | Left Iliac | Right Iliac |
| PK | N/A | 8 days | 66 | DEB | DEB |
| | N/A | | 67 | DEB | DEB |
| | N/A | | 68 | DEB | DEB |
| | N/A | 1 day | 69 | DEB | DEB |
| | N/A | | 70 | DEB | DEB |
| | N/A | | 71 | DEB | DEB |
| | N/A | 14 days | 72 | DEB | DEB |
| | N/A | | 73 | DEB | DEB |
| | N/A | | 74 | DEB | DEB |
| LM | 23640 | 28 days | 75 | Non-DEB | DEB |
| | 23641 | | 76 | DEB | Non-DEB |
| | 23642 | | 77 | Non-DEB | DEB |
| | 23643 | | 78 | DEB | Non-DEB |
| | 23644 | | 79 | Non-DEB | DEB |
| | 23645 | | 80 | DEB | Non-DEB |
| | 23646 | | 81 | Non-DEB | DEB |
| | 23647 | | 82 | DEB | Non-DEB |

FIG. 4

| Parameter | Animal | Mean | Std. Deviation | P-Value Kruskal Wallis Test |
|---|---|---|---|---|
| Luminal Area Average | Control | 4,68 | 1,92 | 0.5 |
| | Sirolimus | 4,41 | 1,53 | |
| | Paclitaxel | 3,71 | 1,50 | |
| Stent Area Average | Control | 6,95 | 1,10 | 0.3 |
| | Sirolimus | 6,24 | 1,11 | |
| | Paclitaxel | 7,07 | 0,68 | |
| NIH average | Control | 2,27 | 1,30 | 0.048 |
| | Sirolimus | 1,83 | 0,75 | |
| | Paclitaxel | 3,36 | 1,07 | |
| NIH Percent Obstr Average | Control | 0,34 | 0,21 | 0.2 |
| | Sirolimus | 0,31 | 0,15 | |
| | Paclitaxel | 0,48 | 0,17 | |

FIG. 5

| Parameter | Animal | Mean | Std. Deviation | P-Value Kruskal Wallis Test |
|---|---|---|---|---|
| Luminal Area Median | Control | 4,74 | 1,89 | 0.5 |
| | Sirolimus | 4,39 | 1,51 | |
| | Paclitaxel | 3,66 | 1,53 | |
| Stent Area Median | Control | 6,94 | 1,12 | 0.4 |
| | Sirolimus | 6,20 | 1,11 | |
| | Paclitaxel | 6,98 | 0,55 | |
| NIH Median | Control | 2,27 | 1,30 | 0.09 |
| | Sirolimus | 1,80 | 0,74 | |
| | Paclitaxel | 3,37 | 1,26 | |
| NIH Percent Obstr Median | Control | 0,33 | 0,21 | 0.2 |
| | Sirolimus | 0,30 | 0,14 | |
| | Paclitaxel | 0,49 | 0,19 | |

FIG. 6

| Parameter | Animal | Mean | Std. Deviation | P-Value Kruskal Wallis Test |
|---|---|---|---|---|
| Luminal Area Minimal | Control | 4,20 | 1,97 | 0.6 |
| | Sirolimus | 3,89 | 1,60 | |
| | Paclitaxel | 3,12 | 1,60 | |
| Stent Area Minimal | Control | 6,61 | 0,89 | 0.5 |
| | Sirolimus | 5,93 | 1,14 | |
| | Paclitaxel | 6,43 | 0,80 | |
| NIH Minimal | Control | 1,93 | 1,37 | 0.3 |
| | Sirolimus | 1,33 | 0,75 | |
| | Paclitaxel | 2,41 | 1,27 | |
| NIH Percent Obstr Minimal | Control | 0,30 | 0,22 | 0.5 |
| | Sirolimus | 0,23 | 0,13 | |
| | Paclitaxel | 0,36 | 0,17 | |

FIG. 7

| Parameter | Animal | Mean | Std. Deviation | P-Value Kruskal Wallis Test |
|---|---|---|---|---|
| Luminal Area Maximal | Control | 4,99 | 1,98 | 0.7 |
| | Sirolimus | 4,98 | 1,54 | |
| | Paclitaxel | 4,40 | 1,41 | |
| stent Area Maximal | Control | 7,28 | 1,26 | 0.4 |
| | Sirolimus | 6,64 | 1,16 | |
| | Paclitaxel | 7,92 | 1,38 | |
| NIH Maximal | Control | 2,66 | 1,25 | 0.02 |
| | Sirolimus | 2,32 | 0,93 | |
| | Paclitaxel | 4,39 | 1,21 | |
| NIH Percent Obstr Maximal | Control | 0,40 | 0,22 | 0.2 |
| | Sirolimus | 0,39 | 0,18 | |
| | Paclitaxel | 0,59 | 0,19 | |

METHOD AND A BALLOON CATHETER ASSEMBLY FOR TREATING BIFURCATION LESIONS

RELATED APPLICATIONS

This application is a continuation-in-part of copending U.S. patent application Ser. No. 13/124,119 filed Jan. 17, 2011, a National Phase Entry Application under 35 U.S.C. §371 of International Application PCT/IN2011/00032 filed Jan. 17, 2011, which designates the U.S. and which claims benefit of priority under 35 U.S.C. §119(b) and 37 CFR 1.55(a) of India Patent Application No. 176/MUM/2010 filed Jan. 22, 2010; and this application is also a continuation-in-part of copending U.S. patent application Ser. No. 12/920,812 filed May 21, 2010, a National Phase Entry Application under 35 U.S.C. §371 of International Application PCT/IN10/00349 filed May 21, 2010, which designated the U.S. and which claims benefit of priority under 35 U.S.C. §119(b) and 37 CFR 1.55(a) of India Patent Application No. 1337/MUM/2009 filed Jun. 2, 2009, all of these incorporated herein by reference in their entirety.

FIELD OF THE INVENTION

The invention generally relates to a method and a balloon catheter assembly and stents for treating bifurcation lesions of a main branch and a side branch of a blood vessel bifurcation. More specifically, the invention relates to a drug delivery system for delivering one or more drugs to the bifurcation lesions in the main branch and the side branch of the blood vessel bifurcation.

BACKGROUND OF THE INVENTION

The current methods for treatment of bifurcation lesions include V-stenting, simultaneous kissing stent technique, kissing balloon technique, stent deployment in a main branch followed by angioplasty of a side branch, Drug Eluting Stents (DESs) specially designed for the bifurcation lesions, T-stenting, crush technique, provisional stenting and the like. The current methods of treatment of bifurcation lesions involve use of medical devices specially designed for use in the bifurcation such as, Bare Metal Stents (BMSs), DESs, Drug Eluting Balloons (DEBs) and angioplasty balloons.

When the BMSs are used for treating the bifurcation lesions, generally, the BMSs are deployed only in the main branch. The side branch is subjected to angioplasty or is left unattended. Alternatively, the BMSs are deployed in both the main branch and the side branch. Deploying the BMSs in both the main branch and the side branch may lead to metal overload in the bifurcation. The metal overload may further result in inflammation and thrombus formation. Also, owing to the complicated structure of the bifurcation, the BMSs may not be appropriate for treating the bifurcation lesions. Therefore, use of DEBs and DESs has gained significance in treatment of the bifurcation lesions.

However, the currently used DEBs and DESs use polymer for loading the drugs on surfaces of the DEBs and the DESs. Owing to the use of polymers, the currently used DEBs and DESs are associated with phenomenon like an inflammation, restenosis, an acute thrombus formation, a sub-acute thrombus formation and a late thrombus formation. Furthermore, in case of the DESs, the amount of drug that is supplied to the lesions generally depends on a metal to artery ratio. The metal to artery ratio of the currently used DESs is 10% to 20%. Therefore, only 10% to 20% of a portion of the lesions is supplied with the drug. In addition, because of the complicated structure of the bifurcation, the metal to artery ratio in case of the bifurcation is generally less than the metal to artery ratio in a general non-bifurcated artery.

In some instances, where the DEBs are used for treating the bifurcation lesions, the time for which the DEBs are exposed to the target site ranges from 30 to 90 seconds. The DEBs have to deliver an effective amount of the drug within these 30 to 90 seconds. In order to deliver the effective amount of the drug within these 30 to 90 seconds, a high amount of the drug has to be loaded on the DEBs. Even after loading a high amount of the drug, the DEBs may not deliver the desired amount of the drug in a short time of 30 to 90 seconds. Further, currently used DEBs can be loaded only with certain highly lipophilic drugs such as, paclitaxel. Whereas, the DEBs that can be loaded with a wider range of drugs are not available in the art.

Additionally, in the currently used DEBs, a drug is coated on the surface of the balloon when the balloon is in a folded configuration. Therefore, a substantial portion of the DEB remains uncoated with the drug. When the DEB is inflated, the portion of the lesion that is exposed to the uncoated portion of the DEB is not supplied with the drug. Therefore, the currently used DEBs may not adequately cover the entire portion of the bifurcation lesions.

Further, the particle size of the drugs as well as the polymers that are coated on the DESs and the DEBs are larger than the size of tissue pores at a target site. Therefore, a substantial amount of drug remains unabsorbed. The unabsorbed drug may be washed away in blood stream and may produce side effects.

Therefore, there is a need in the art for an improved drug-delivering insertable medical device for treating the bifurcation lesions that is associated with reduced instances of restenosis, acute thrombus formation, sub-acute thrombus formation, and late thrombus formation. Further, there is need in the art for an improved drug-delivering insertable medical device that can deliver a desired amount of drug to the bifurcation lesions within 30 to 90 seconds with an optimum loading of the drug.

DETAILED DESCRIPTION

This disclosure describes a balloon catheter assembly for delivering nano-carriers to bifurcation lesions in one or more of a main branch and a side branch of a blood vessel bifurcation within 30 to 90 seconds. The balloon catheter assembly includes two or more balloons designed for use in the blood vessel bifurcation. The balloon catheter assembly may also include one or more stents. A surface of one or more of the two or more balloons is coated with the nano-carriers. Stents, when included, may also be coated with the nano-carriers. The nano-carriers include one or more drugs encapsulated with one or more biological agents.

Before describing in detail embodiments that are in accordance with the invention, it should be observed that the embodiments reside primarily in combinations of components of a drug delivery system. Accordingly, the components have been described to include only those specific details that are pertinent to understanding the embodiments of the invention so as not to obscure the disclosure with details that will be readily apparent to those of ordinary skill in the art having the benefit of the description herein.

In this document, the terms "comprises," "comprising," or any other variation thereof, are intended to cover a non-exclusive inclusion, such that a process, method, or device, that comprises a list of elements does not include only those elements but may include other elements not expressly listed or inherent to such process, method, or device. An element preceded by "comprises . . . a" does not, without more constraints, preclude the existence of additional identical elements in the process, method, article, or apparatus that comprises the element.

Further, before describing in detail embodiments that are in accordance with the invention, it should be observed that all the scientific and technical terms used in for describing the invention have same meanings as would be understood by a person skilled in the art. The term "bifurcation" means a structure of a blood vessel where the blood vessel is divided into a main branch and a side branch. The term main branch means the blood vessel from which the side branch originates. Further, the term "bifurcation lesions" means the lesions present in one or more of the main branch, the side branch and a trunk of a blood vessel bifurcation.

Pursuant to various embodiments, the invention discloses a drug delivery system for delivering one or more drugs to one or more of a first branch and a second branch of a blood vessel bifurcation. The first branch may be the main branch of the of the blood vessel bifurcation. Alternatively, the first branch may include a trunk and the main branch of the blood vessel bifurcation. Whereas, the second branch may be one or more of the side branch and the trunk of the blood vessel bifurcation.

Further, one or more of the first branch and the second branch may have one or more of one or more lesions, one or more thrombus and one or more injuries. The one or more of the first branch and the second branch having one or more of one or more lesions, one or more thrombus and one or more injuries are hereinafter referred to as a target site. However, the target site may include any area inside the blood vessel bifurcation to which the one or more drugs may be delivered using the drug delivery system without departing from the scope of the invention.

The drug delivery system includes a first balloon catheter assembly having a first balloon capable of passing through the blood vessel and being at least partially positioned in the first branch. The drug delivery system further includes a second balloon catheter assembly having a second balloon capable of passing through the blood vessel and being at least partially positioned in the second branch. One or more of the first catheter assembly and the second catheter assembly may include an angioplasty/angiography catheter and a thrombus aspiration catheter. The first balloon and the second balloon may be positioned at the target site in the main branch and the side branch respectively using methods and techniques known in the art. Thereafter, the first balloon and the second balloon may be inflated using methods and techniques known in the art.

The first catheter assembly includes a catheter, a guide wire passing through the catheter, the first balloon mounted on a distal end of the catheter, and a mechanism for infusing fluid into the first balloon to inflate the first balloon. Similarly, second catheter assembly includes a catheter, a guide wire passing through the catheter, the second balloon mounted on a distal end of the catheter, and a mechanism for infusing fluid into the second balloon to inflate the second balloon. Alternatively, the drug delivering system may include a catheter assembly having a first catheter and a second catheter, a first guide wire and a second guide wire passing through the first catheter and the second catheter respectively, and a first balloon and a second balloon mounted on the first catheter and the second catheter respectively.

In accordance with various embodiments, the first balloon may have one or more of a shape, a size and dimensions different from the second balloon. For example, the first balloon may have a conical shape with a proximal diameter smaller than a distal diameter of the first balloon. Whereas, the second balloon may have a proximal diameter smaller than or equal to a distal diameter of the second balloon. As such, the second balloon may have one of a conical shape and a cylindrical shape. Thus, owing to one or more of, different shapes, dimensions and sizes of the first balloon and the second balloon, distention of the trunk of the blood vessel bifurcation is prevented. This in turn prevents inflammation and injury to the blood vessel bifurcation.

In an exemplary embodiment, the first balloon may have a generally conical shape with a tapering proximal portion. The tapering proximal portion may have a smaller diameter as compared to the diameter of a distal portion of the first balloon. Thus, the distal portion of the first balloon is suitable for being inserted into the side branch. Once inserted and positioned in the side branch, the first balloon is inflated. Whereas, a proximal portion of a second balloon of the two balloons may have a diameter equal to or greater than the diameter of a distal portion of the second balloon. Thus, the distal portion of the second balloon is suitable for being inserted and inflated in a distal portion of the main branch of the blood vessel bifurcation.

Figure 1:
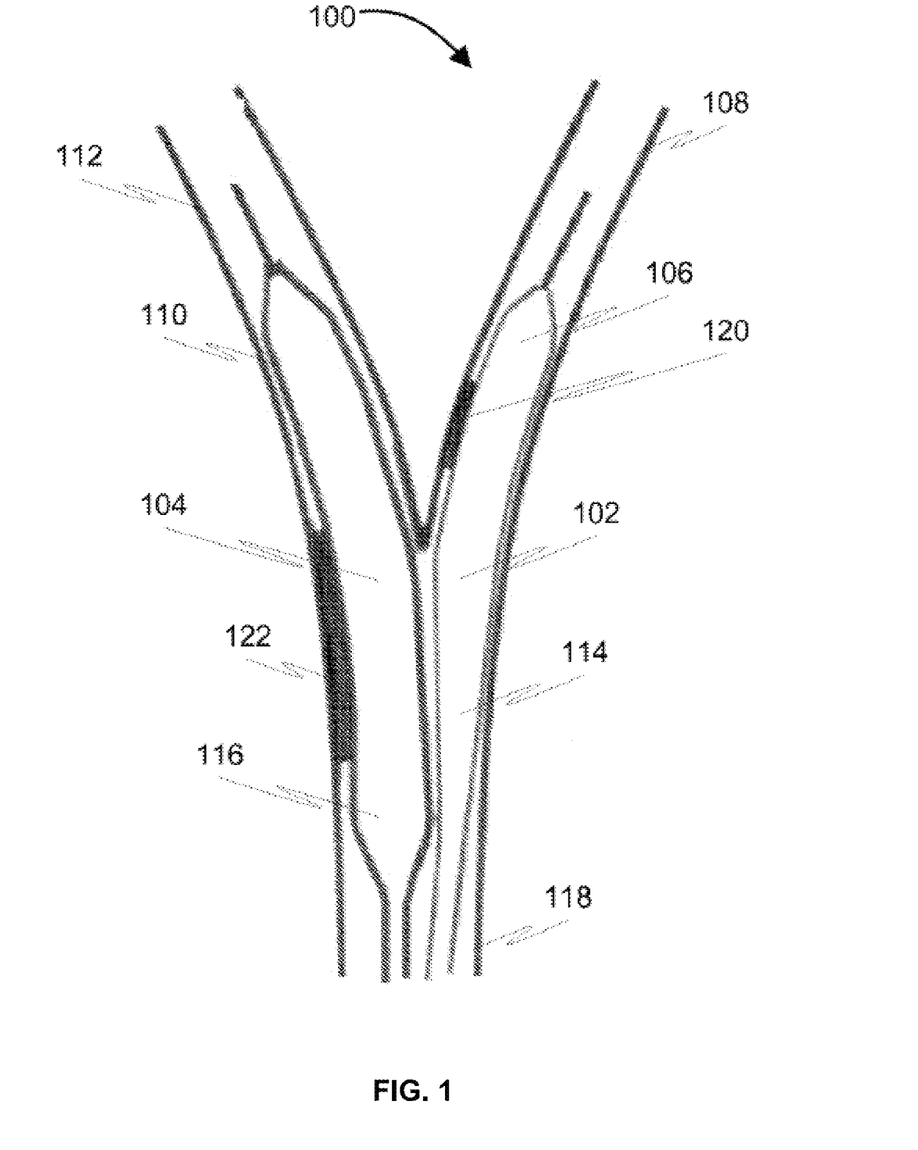
FIG. 1 illustrates a schematic diagram showing a first balloon and a second balloon positioned in a main branch and a side branch of a blood vessel bifurcation in accordance with an embodiment of the invention.

FIG. 1 illustrates a schematic diagram showing a first balloon and a second balloon positioned in a main branch and a side branch of a blood vessel bifurcation in accordance with an embodiment of the invention. As illustrated in FIG. 1, a blood vessel bifurcation 100 has a first balloon 102 and a second balloon 104 positioned and inflated therein. A distal portion 106 of first balloon 102 is positioned in a side branch 108 and a distal portion 110 of second balloon 104 is positioned in a distal portion of main branch 112. Whereas, a proximal portion 114 of first balloon 102 and a proximal portion 116 of second balloon 104 are positioned side by side in a trunk 118 of blood vessel bifurcation 100. Trunk 118 in this case is a common artery. Thus, owing to the different proximal and distal diameters of one or more of the two balloons, distention of the common artery upon inflation of the first balloon and the second balloon may be avoided. When distal portion 106 of first balloon 102 and distal portion 110 of second balloon 104 comes in contact with a first lesion 120 and a second lesion 122, the one or more drugs (not illustrated in FIG. 1) are delivered to first lesion 120 and second lesion 122 respectively.

In an embodiment, one or more of the first balloon and the second balloon may include a stepped balloon. A stepped balloon may have a proximal diameter smaller than a distal diameter. Alternatively, one or more of the first balloon and the second balloon may include any balloon with a shape that prevents distention of the common artery when the first balloon and the second balloon are positioned and inflated in the blood vessel bifurcation.

Further, one or more of one or more portions of the first balloon and one or more portions of the second balloon are coated with a plurality of nano-carriers. A nano-carrier of the plurality of nano-carries (hereinafter referred to as "nano-carriers") includes one or more drugs encapsulated with one or more biological agents. In an embodiment, a nano-carrier may include one or more of nano-crystals and micro-crystals of the one or more drugs surrounded by one or more of nano-particles and micro particles of the one or more biological agents.

The one or more drugs may include, but not limited to, one or more of an anti-proliferative agent, an anti-inflammatory agent, an anti-neoplastic agent, an anti-coagulant agent, an anti-fibrin agent, an antithrombotic agent, an anti-mitotic agent, an antibiotic agent, an anti-allergic agent, an antioxidant, one or more flavonoids, an estrogen, a protease inhibitor, an antibody, an immunosuppressive agent, a cytostatic agent, a cytotoxic agent, a calcium channel blocker, a phosphodiesterase inhibitor, a prostaglandin inhibitor, a dietary supplement, a vitamin, an anti-platelet aggregating agent, and genetically engineered epithelial cells. The one or more flavonoids are selected from at least one of narigenin, naringin, eriodictyol, hesperetin, hesperidin (esperidine), kampferol, quercetin, rutin, cyanidol, meciadonol, catechin, epi-gallo-catechin-gallate, taxifolin (dihydroquercetin), genistein, genistin, daidzein, biochanin, glycitein, chrysin, diosmin, luetolin, apigenin, tangeritin and nobiletin.

Examples of the one or more drugs include, but not limited to, one or more of sirolimus, paclitaxel, tacrolimus, clobetasol, dexamethasone, genistein, heparin, beta-estradiol, rapamycin, everolimus, ethylrapamycin, zotarolimus, ABT-578, Biolimus A9, docetaxel, methotrexate, azathioprine, vincristine, vinblastine, fluorouracil, doxorubicin hydrochloride, mitomycin, sodium heparin, low molecular weight heparin, heparinoid, hirudin, argatroban, forskolin, vapiprost, prostacyclin, prostacyclin analogues, dextran, D-phe-pro-arg-chloromethylketone, dipyridamole, glycoprotein IIb/IIIa, recombinant hirudin, bivalirudin, nifedipine, colchicines, lovastatin, nitroprusside, suramin, serotonin blockers, a steroid, thioprotease inhibitors, triazolopyrimidine, nitric oxide, nitric oxide donors, super oxide dismutase, super oxide dismutase mimetics, estradiol, aspirin, angiopeptin, captopril, cilazapril, lisinopril, permirolast potassium, alpha-interferon, and bioactive RGD and any salts or analogues thereof. In an embodiment, the one or more drugs are one of a sirolimus (rapamycin) and paclitaxel.

Whereas, a biological agent of the one or more biological agents may include one or more of, but are not limited to, drug carriers, excipients, blood components, excipients derived from blood, phospholipids, solid lipid nano-particles, lipoids, vitamins and sugar molecules. Examples of the one or more biological agents may include, but are not limited to, a steroid, a vitamin, an estradiol, an esterified fatty acid, a non-esterified fatty acid, glucose, inositol, L-lactate, a lipoprotein, a carbohydrate, tricalcium phosphate, precipitated calcium phosphate, a substance derived from at least one of human, egg and soybean, phospholipon 80H, phospholipon 90H, Lipoid S75, Lipoid E80, Intralipid 20, Lipoid EPC, Lipoid E75, a lipid obtained from egg, a lipid obtained from soya, phosphatidylcholine, phosphatidylglycerol, phosphatidylinositol, phosphatidylserine, phosphatidic acid, cardiolipin, and phosphatidylethanolamine. In an embodiment, the one or more biological agents are one of a phospholipid and Lipoid E80.

Further, the one or more biological agents may exhibit one or more effects. The one or more effects include stabilizing the one or more drugs and affinity for tissues at the target site in the blood vessel bifurcation. Owing to the affinity of the one or more biological agents towards the tissues, the nano-carriers are rapidly absorbed by the tissues as compared to nano-particles containing a drug encapsulated by a polymer. The one or more biological agents may be soluble in a pH below 7.4. Therefore, when the nano-carriers come in contact with the tissues at the target site, the one or more biological agents are dissolved in the blood. The dissolution of the one or more biological agents results in release of the one or more drugs at the target site. Thus, a pH dependent release of the one or more drugs from the nano-carriers is achieved.

The nano-carriers may include the nano-crystals of the one or more drugs encapsulated with the nano-particles of the one or more biological agents. The surface of the nano-carriers is devoid of the drug. The nano-carriers may be coated on one or more of the first balloon and the second balloon when they are in an unfolded configuration. Alternatively, the nano-carriers may be coated on the one or more of the first balloon and the second balloon when they are in a folded configuration.

The nano-carriers may have an average diameter ranging from 10 nm to 5000 nm. Alternatively, the nano-carriers may include two or more sets of nano-carriers having two or more different average diameters. More specifically, the nano-carriers may include a first set of nano-carriers with a first average diameter and a second set of nano-carriers with a second average diameter. The first average diameter is different from the second average diameter. For example, the first average diameter may range from 10 nm to 700 nm and the second average diameter may range from 300 nm to 1000 nm.

In an embodiment, the nano-carriers may include a first set of nano-carriers with a first average diameter, a second set of nano-carriers with a second average diameter, and a third set of nano-carriers with a third average diameter. The first average diameter may range from 10 nm to 500 nm, the second average diameter may range from 300 nm to 800 nm, and the third average diameter may range from 500 nm to 1000 nm. Any number of different sets of nano-carriers with varying average diameters may be used to achieve a particular therapeutic object without departing from the scope of the invention.

For example, one or more of the first balloon and the second balloon are coated with a first set of nano-carriers, a second set of nano-carriers and a third set of nano-carriers. When the one or more of the first balloon and the second balloon are inflated and positioned in the blood vessel bifurcation, the first set of nano-carriers, the second set of nano-carriers and the third set of nano-carriers are released from the one or more of the first balloon and the second balloon. Thereafter, the first set of nano-carriers, the second set of nano-carriers and the third set of nano-carriers penetrate the tissue layers of the blood vessel bifurcation. The first set of nano-carriers includes nano-carriers having a first average diameter suitable for penetrating an intima layer of the blood vessel bifurcation. The second set of nano-carriers includes nano-carriers having a second average diameter suitable for penetrating a media layer of the blood vessel bifurcation through the intima layer and a vasa vasorum associated with the media layer. Further, the third set of nano-carriers includes nano-carriers with a third average diameter suitable for penetrating an adventitia layer of the blood vessel bifurcation through the intima layer and the vasa vasorum associated with the media layer and a vasa vasorum associated with the adventitia layer.

In an embodiment, one or more of the first balloon and the second balloon have a hydrophilic surface and a non-hydrophilic surface. The hydrophilic surface may include any lubricous coating applied on the surface of one or more of the two balloons. Examples of the lubricious coating include, but are not limited to, polyalkylene glycols, alkoxy polyalkylene glycols, copolymers of methylvinyl ether and maleic acid poly (vinylpyrrolidone), poly(N-alkylacrylamide), poly(acrylic acid), poly(vinyl alcohol), poly(ethyleneimine), methyl cellulose, carboxymethyl cellulose, polyvinyl sulfonic acid, heparin, dextran, modified dextran and chondroitin sulphate and at least one anti-block agent.

The hydrophilic surface may include one or more exposed hydrophilic surfaces. The one or more exposed hydrophilic surfaces may be created at one or more desired portions of an inflatable balloon such as, the first balloon and the second balloon, by not coating the nano-carriers on the one or more desired portions. In other words, the nano-carriers are coated on the entire hydrophilic surface except the one or more exposed hydrophilic surfaces. In an embodiment, the one or more exposed hydrophilic surfaces are created at one or more of one or more portions of a distal end of the hydrophilic surface and one or more portions of a proximal end of the hydrophilic surface.

As such, the one or more exposed hydrophilic surfaces facilitate dissolution of the lubricious coating upon coming in contact with the blood at the target site. In response to the dissolution of the lubricious coating, the nano-carriers are released at the target site from the hydrophilic surface. Thus, the one or more exposed hydrophilic surfaces facilitate the release of the nano-carriers from the two balloons.

When one or more of the two balloons are inflated at the target site, about 30% to 80% of the nano-carriers are released from the hydrophilic surface within 15 to 90 seconds. The nano-carriers coated on one or more portions of the hydrophilic surface are released rapidly as compared to the release of nano-carriers from the surface of a balloon without the lubricious coating. Thus, a burst release of the nano-carriers from the hydrophilic surface may be achieved within a short period for which the two balloons come in contact with the target site in the blood vessel bifurcation. In an exemplary embodiment, about 70% to 80% of the nano-carriers are released from the hydrophilic surface within about 60 seconds when the first balloon and the second balloon are inflated at the target site.

In another embodiment, one or more of the first balloon and the second balloon are coated with an outer layer of nano-carriers and an inner layer of nano-carriers. The outer layer may include the third set of nano-carriers. The inner layer may include one or more of the second set of nano-carriers and the first set of nano-carriers. Further, a drug present in the outer layer may be same or different from a drug present in the inner layer. In an exemplary embodiment, the drug present in the outer layer is an anti-inflammatory agent. Whereas, the drug present in the inner layer may include one or more of an anti-thrombogenic agent and an anti-proliferative agent.

In accordance with various embodiments, the first set of nano-carriers and the second set of nano-carriers may include a same or a different drug. In addition, the second set of nano-carriers and the third set of nano-carriers may include a same or a different drug. Further, an average diameter of the first set of nano-carriers may range from 800 nm to 1500 nm, an average diameter of the second set of nano-carriers may range from 300 nm to 800 nm and an average diameter of the third set of nano-carriers may range from 10 nm to 300 nm.

In yet another embodiment, a surface of one or more of the first balloon and the second balloon has a hydrophilic layer coated on the surface. The nano-carriers are coated on one or more portions of the hydrophilic layer. The hydrophilic layer enables release of the nano-carriers from the hydrophilic layer within 30 to 90 seconds when the one or more of the two balloons are inflated at the target site. Alternatively, the hydrophilic layer is coated with a second layer. The second layer includes one or more of the biological agents and a polymer. Further, one or more pores are present in the second layer and one or more nano-carriers of the nano-carriers are deposited in the one or more pores. When one or more of the first balloon and the second balloon are inflated upon coming in proximity of the target site in the blood vessel bifurcation, the one or more nano-carriers are released from the one or more pores.

In an embodiment, one or more nano-carriers of the plurality of nano-carriers further include nano-particles of the one or more drugs encapsulated with nano-particles of the one or more biological agents and nano-particles of one or more polymers. The one or more polymers include one or more of a biodegradable polymer, a non-degradable polymer, a bioerodable polymer, an excipient, a drug, and a polymer matrix. Examples of the one or more polymers include, but are not limited to, poly(1-lactide), racemic polylactide, poly (1-lactide-co-glycolide), racemic poly(1-lactide-co-glycolide), poly(1-lactide-co-caprolactone poly(d,l-lactide-co-caprolactone), poly(1-lactide-co-trimethylene carbonate) and poly(d,l-lactide-co-trimethylene carbonate). When the one or more polymers and the one or more biological agents are used to encapsulate the one or more drugs, the one or more polymers may be covalently attached to one or more of the one or more drugs and the one or more biological agents.

In another embodiment, the nano-carriers, the nano-particles of the one or more drugs, the nano-particles of the one or more biological agents, and one or more excipients are deposited in a polymer matrix coated on at least one of the hydrophilic surface and the non-hydrophilic surface.

EXAMPLES

Example 1

Preparation of the Nano-Carriers

Lipoid E80 was obtained from Lipoid GMBH, Batch No.: 776114-1/906. Sirolimus was obtained from Biocon Ltd. (India), Batch No.: EH-B10-01-000982/01337. The water, other solvents and reagents used were of HPLC grade. A polyamide catheter system (Yangtze .mu.sup.sb PTCA cathater) with COPAN Co-Polyamide dedicated angioplasty balloons for blood vessel bifurcation (hereinafter referred to as "the balloon system") coated with Hydraflow®. Hydrophilic coating (hereinafter referred to as "the hydrophilic surface") was obtained from Minvasys, Paris, France.

Figure 2:
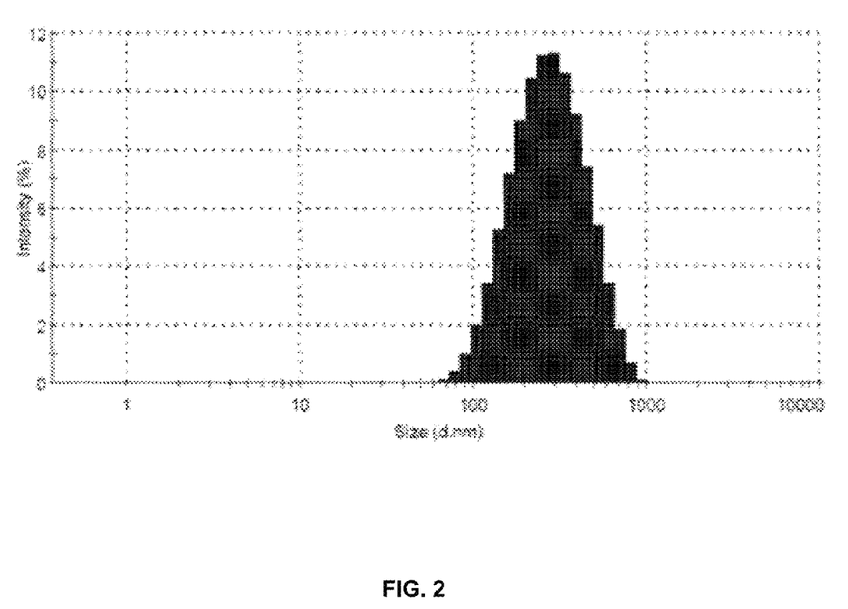
FIG. 2 illustrates size distribution of nano-particles of Lipoid E80 as detected by Malvern Zeta Sizer (ZS90) in accordance with Example 1.

Lipoid E80 was dissolved in methanol. 100 ml HPLC grade water and Tween 80 (5 mg) was added to obtain an aqueous solution of Lipoid E80. The aqueous solution Lipoid E80 (10 ml) was subjected to ultrasonic homogenization for 20 to 25 minutes in an ice-cold water bath to obtain Solution A1. The Solution A1 thus obtained contained nano-particles of Lipoid E80. The solution A1 was subsequently analyzed for particle size detection using Malvern Zeta Sizer (ZS90) [Malvern, UK] size detector. FIG. 2 illustrates the size distribution of nano-particles of Lipoid E80 as detected by Malvern Zeta Sizer (ZS90). Z-average diameter of the nano-particles of the Lipoid E80 was found to be 242.8074 nm.

Sirolimus (20 mg) was dissolved in minimum quantity of methanol. HPLC grade water containing 0.5% w/w of Tween 80 was added to obtain an aqueous solution of sirolimus by re-precipitation. The aqueous solution of sirolimus (100 ml) was subjected to ultrasonic homogenization for 100 to 200 minutes in an ice-cold water bath to obtain Solution A2. The Solution A2 thus obtained contained nano-crystals of sirolimus. The solution A2 was subsequently analyzed for particle size detection using Malvern ZS90 (Malvern, UK) size detector.

Figure 3:
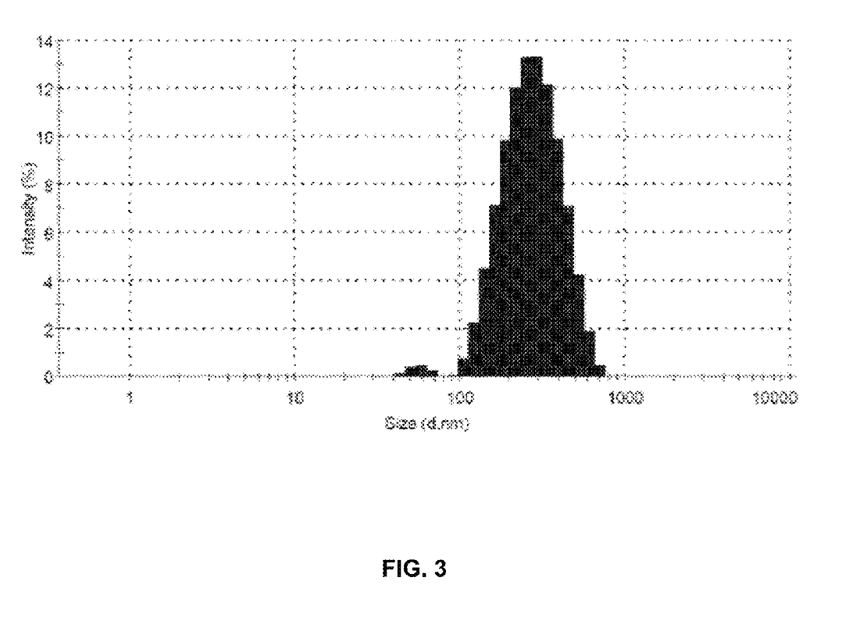
FIG. 3 illustrates size distribution of the nano-carriers as detected by Malvern ZS90 in accordance with Example 1.

10 ml solution A1 was added to Solution A2 drop by drop slowly under a ultrasonic homogenization process. The resultant mixture was subjected to ultrasonic homogenization for another 20 minutes after complete addition to obtain Solution A3. Solution A3 was then stirred with a magnetic stirrer (2MLH hot plate heater cum stirrer, Accumax, INDIA) for 20 minutes. Solution A3 thus obtained contained nano-carriers (nano-crystals of sirolimus surrounded by nano-particles of Lipoid E80). Solution A3 was subsequently analyzed for particle size detection using Malvern ZS90 (Malvern, UK) size detector. FIG. 3 illustrates size distribution of the nano-carriers as detected by Malvern Z590. The average diameters of nano-carriers were found to be 245.493 nm.

Solution A3 (Aqueous solution of nano-carriers) was further subjected to extraction with dichloromethane. Solution A3 (about 100 ml) was transferred to a 250 ml separating funnel. 50 ml of dichloromethane was added to the 250 ml separating funnel. The resultant mixture was shaken for 15 minutes and then allowed to stand. Thereafter, two layers i.e., an aqueous layer and a dichloromethane layer were observed in the 250 ml separating funnel. The dichloromethane layer was separated from the aqueous layer. The solution was evaporated up to a volume of 50 ml. The dichloromethane layer i.e., solution of the nano-carriers was stored in an amber colored small measuring flask with a batch number. Subsequently, the solution of the nano-carriers was used for coating the balloon system.

Example 2

Preparation of the Drug Delivery System (The Balloon System)

Yangtze .mu.sup.b PTCA catheter of the size 2.5 mm*10 mm was used for the coating. The solution of the nano-carriers (about 3 ml) was fed into reservoir of a coating machine. The balloons of the balloon system were mounted on a rotating mandrel of the coating machine one by one. Each balloon of the balloon system was exposed to an atomization nozzle of the coating machine separately. The balloon system was rotated at a speed varying from 5 rpm to 40 rpm by rotating the mandrel. Simultaneously, the solution of nano-carriers was sprayed over the balloons at an inert gas pressure varying from 0.5 psi to 4.0 psi in two oscillations. Thus, the balloons coated with the nano-carriers (hereinafter referred to as "the coated balloon system") was obtained. The coated balloon system was then removed and checked under a high-resolution microscope for the coating surface smoothness and any foreign particles.

Various embodiments of the invention provide a medical device and a method for delivering one or more drugs to bifurcation lesions in a main branch and a side branch of the blood vessel bifurcation within 30 to 90 seconds. Further, the invention provides a medical device specially designed for treating the bifurcation lesions that is associated with reduced instances of a restenosis, an acute thrombus formation, a sub-acute thrombus formation, and a late thrombus formation.

In an embodiment, the inflatable balloon is used to deliver the drug to a target site where a stent is deployed in the blood vessel. In such an instance, owing to the in-tissue release and in-tissue penetration of the drug for the prolonged time, the instances of delayed healing of lesions at the target site and improper healing of the lesions at the target site are minimized. Thus, an anti-platelet therapy that has to be given to the patients with delayed healing or improper healing of the lesions may be minimized.

Example 3

Figure 4:
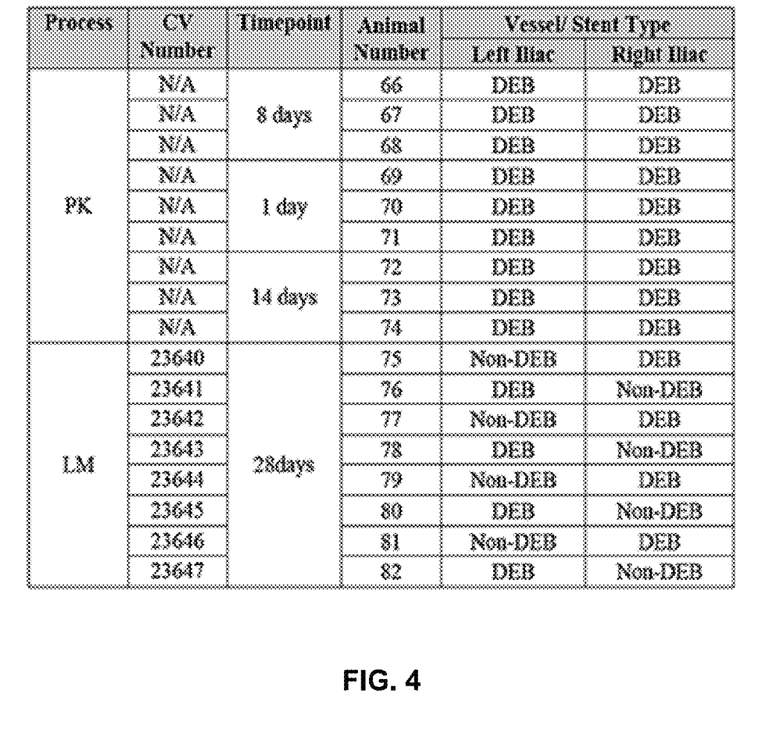
FIG. 4 is a table illustrating numbers assigned to 17 animals, stent type and location of stent in each animal and the type of study (PK/LM) conducted on the animals in accordance with Example 3.

A coated balloon was evaluated in-vivo in 17 male New Zealand rabbits, 5 to 6 months old and weighing between 3 and 4 Kg (hereinafter "animals") for PharmacoKinetic (PK) study and histological evaluation or Light Microscopy (LM). FIG. 4 is a table illustrating numbers assigned to 17 animals, stent type and location of stent in each animal and the type of study (PK/LM) conducted on the animals. Out of the 17 animals 9 (Animals 66 to 74) were used for PK study and 8 (Animals 75 to 82) were used for histological evaluation.

The coated balloons were inserted into both the iliofemoral arteries of the animals used for the PK study. The coated balloons were inflated twice in the iliofemoral arteries. The coated balloons were first inflated for 70 seconds at 7 ATM and then deflated. Again, the coated balloons were inflated for the second time for 60 seconds at 7 ATM and then deflated and withdrawn.

A pre-mounted stent (3.0 mm.times.12-14 mm) i.e., a stent mounted on the coated balloon was implanted in the right and the left iliac artery of the animals at a nominal pressure with 30 seconds of balloon inflation. The balloon to stent ratio for all the pre-crimped stents was approximately 1.4:1. Following the deployment of the stents, angiography was performed to examine the patency of the stents.

Whole blood was collected from the central ear of the animals for serum analysis at four time points, namely 0.5

Hour, 1 Hour, 3 Hour and 24 hour post deployment of the stents. After euthanasia at the respective time point, the tissue around the stent was dissected free, weighed, and snapfrozen in liquid nitrogen for later measurement. The University of Colorado Denver performed drug analysis of whole blood and the tissue surrounding the stent. The concentration of sirolimus at the four time points i.e. 0.5 Hour, 1 Hour, 3 Hour and 24 Hour was found to be 9.32 ng/ml, 7.08 ng/ml, 4.09 ng/ml and 0.81 ng/ml, respectively.

It was concluded that at Day 1, Day 8, and Day 14 pharmacokinetics study, maximal blood concentrations of sirolimus were seen at 30 minutes post catheterization (9.3 ng/ml) while circulating levels decreased markedly by 24 hours (0.81 ng/ml). For tissue drug levels, maximal concentrations were achieved at Day 1 (140.4 ng/mg), which showed a significant decreased to 15.5 ng/mg by Day 8 and 5.5 ng/mg by Day 14. Individual drug concentrations at each time point however, show variation among arteries where values at Day 1 ranged from 35.0 to 275.0 ng/mg, values at Day 8 ranged from 0.7 ng/mg to 33.2 ng/mg and values at Day 14 ranged from 14.8 ng/mg to below limits of quantification [BLQ] in two animals (Animal number 72 and 74). In comparison, published data in the rabbit with a sirolimus-eluting stent at similar time points achieved tissue concentrations of 4.52 ng/mg and 1.56 ng/mg at Day 1 and Day 8, respectively (Finn A V, Kolodgie F D Circulation 2005; 112:270).

Further measurements included histological study of the slides of the tissues around the stents. The slides were analyzed by using National Institute for Standard and Technology calibrated microscope system (IP Lab Software, MD). The cross-sectional areas for each slide i.e. External Elastic Lamina (EEL), Internal Elastic Lamina (IEL) and the Lumen Area were measured. Neointimal thickness was measured as a distance between the inner surface of the stent strut and the Luminal border of the stent. Vessel layer areas were calculated using the following formulae:

Area of Media=EEL-IEL,

Neointima Area=IEL-the Lumen Area and

Percent Stenosis=[1−(Luminal Area/IEL)]*100.

All the stents were found to be widely expanded and well apposed to the vessel walls. All the animals survived the in-life-phase of the study.

Re-endothelialization was found to be complete for the sample group and the control group. Percent Stenosis was found to be 11.48 (.+−.1.30%) in sample group and 11.49 (.+−.1.49%) in the control group. The Neointimal Thickness was found to be 0.030 mm (+−.0.0076 mm) in sample group and 0.032 (.+−.0.0098 mm) in the control group.

In-tissue sirolimus concentration was also evaluated at Day 1, Day 8 and Day 14. The in-tissue sirolimus concentration at Day 1, Day 8 and Day 14 were found to be 140.4 ng/mg, 15.5 ng/mg and 5.5 ng/mg respectively. It was concluded that relatively higher in-tissue concentrations can be achieved with the coated balloon with single inflation as compared with the published data of study in rabbits pertaining a sirolimus-eluting stent with similar time points (Finn A V, Kolodgie F D Circulation 2005; 112:270).

Example 4

Six Brazilian pigs (Hereinafter "the animals") weighing about 25 to 30 kg were selected for the study. Bare metal stent (Cronus®, obtained from, Scitech, Brazil), with sizes of stent ranging from 2.5*13 mm to 3.0*13 mm and the coated balloons with sizes of about 3.0*15 mm were used. The stents were deployed in three vessels i.e. LAD (Left Interior Descending), LCX (Left Circumflex) and RCA (Right Coronary Artery of each animal by using: a) the coated balloon (Sirolimus), b) the coated balloon (Paclitaxel) and c) a bare balloon. The Paclitaxel coated balloon was prepared by replacing sirolimus in example 1 with Paclitaxel and rest of the process was kept same. The balloon to artery ratio for each coated balloon was approximately 1.1:1.0 to 1.2:1.0. Each of the coated balloon and the bare balloon were inflated for 60 seconds. The animals with sirolimus coated balloon were labeled "Sirolimus", the animals with Paclitaxel coated balloon were labeled "Paclitaxel" and the animals with bare balloon were labeled "Control".

The groups i.e Sirolimus, Paclitaxel and Control were each studied for qualitative OCT analysis. The qualitative parameters that were studied included: a) Tissue Proliferation at the stent edges, b) Intra-luminal Thrombus Formation and c) Uncovered Stent Struts. It was found that the Tissue Proliferation at the stent edges was found in one Control and two Paclitaxel. Whereas, no incidence of Tissue Proliferation at the stent edges was observed in the Sirolimus group. Further, it was found that the Intra-luminal Thrombus Formation was found in one Control and two Paclitaxel. Whereas, no incidences of Intra-luminal Thrombus Formation were observed in the Sirolimus group.

It was concluded that sirolimus performed better than paclitaxel and bare balloon in terms of reduction in neointimal growth and endothelialization. The stent strut coverage by tissue was virtually complete for all the groups. Toxic effect was found in paclitaxel group. The toxic effect was found in the paclitaxel group due to greater in-tissue concentration of paclitaxel. However, the dose of the paclitaxel used was lower as compare with commercially available products. Thus, the coated balloons showed acute transfer of paclitaxel or sirolimus using a polymer free approach.

Figure 5:
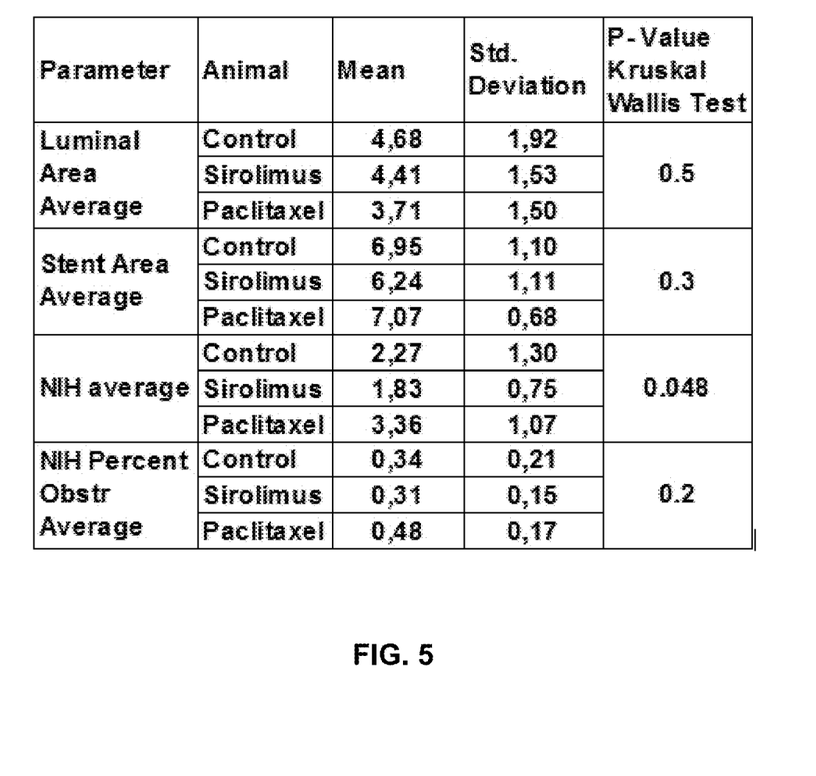
FIG. 5 illustrates a table of values of mean and standard derivations of the Average Luminal Areas, Average Stent Areas, Average Neointimal Areas and Average Percent Neointimal Obstruction findings for each group i.e. Control, Sirolimus and Paclitaxel in accordance with Example 4.
Figure 6:
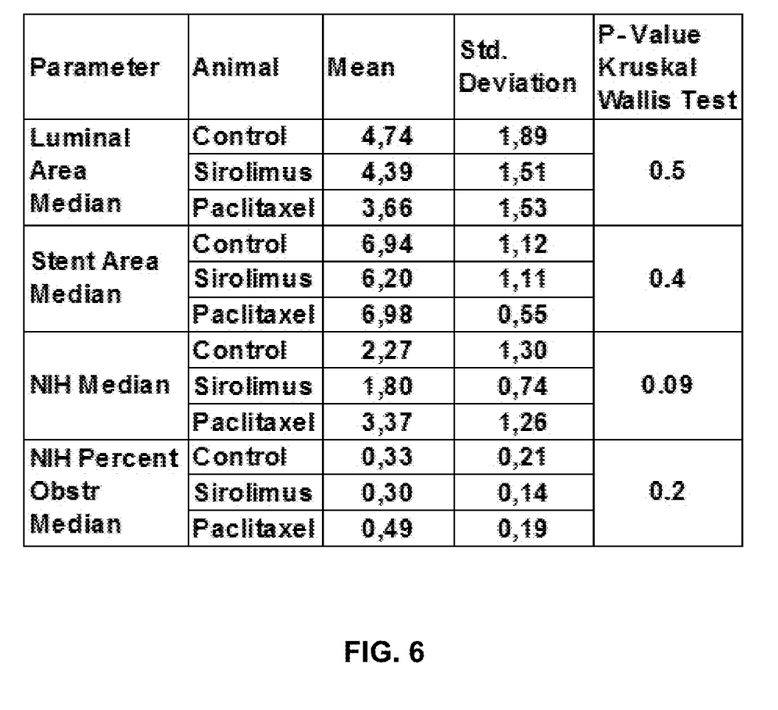
FIG. 6 illustrates a table of values of mean and standard derivations of the Median Luminal Areas, Median Stent Areas, Median Neointimal Areas and Median Percent Neointimal Obstruction findings for each group in accordance with Example 4.
Figure 7:
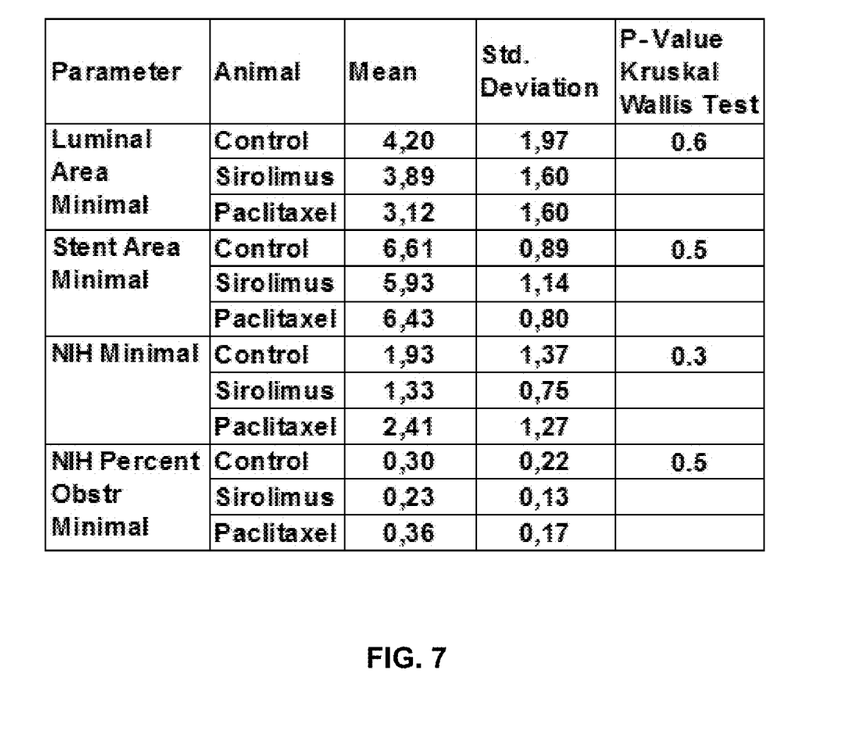
FIG. 7 illustrates a table of values of mean and standard derivations of the Minimal Luminal Areas, Minimal Stent Areas, Minimal Neointimal Areas and Minimal Percent Neointimal Obstruction findings for each group in accordance with Example 4.
Figure 8:
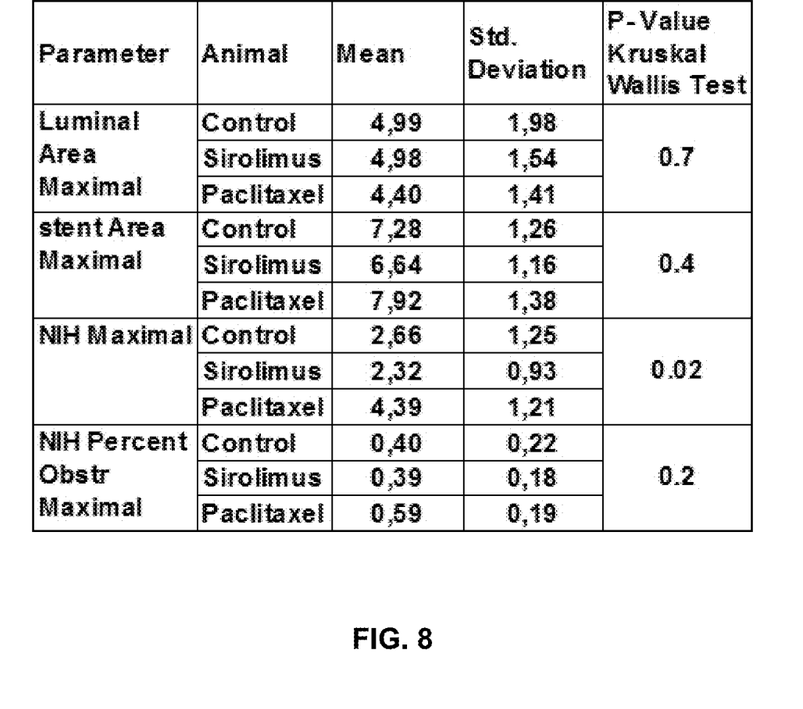
FIG. 8 illustrates a table of values of mean and standard derivations of the Maximal Luminal Areas, Maximal Stent Areas, Maximal Neointimal Areas and Maximal Percent Neointimal Obstruction findings for each group in accordance with Example 4.
Figure 9:
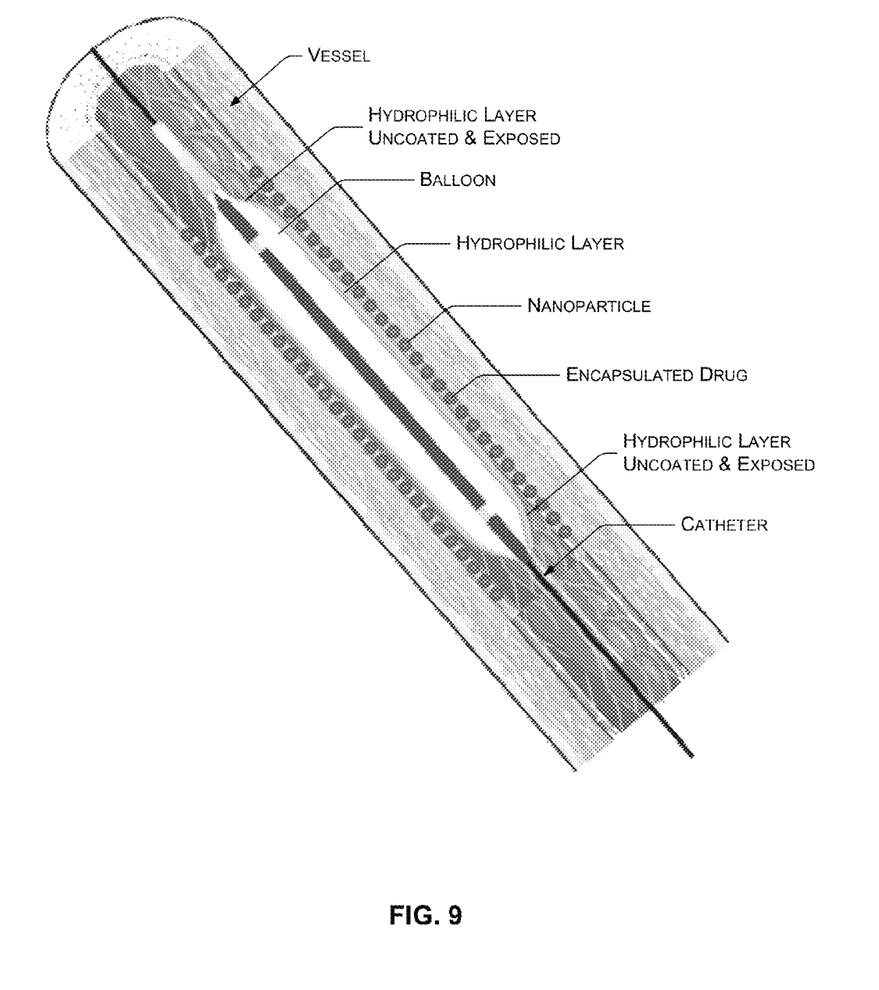
FIG. 9 is a diagram of a drug-delivering medical device shown in a body lumen, that includes a balloon catheter, an inflatable balloon positioned on the balloon catheter, the inflatable balloon having a hydrophilic surface, at least one portion of the hydrophilic surface being coated with a plurality of nano-carriers (nano-carriers not shown to scale), with at least one of the nano-carriers surrounded by an encapsulating medium.
Figure 10:
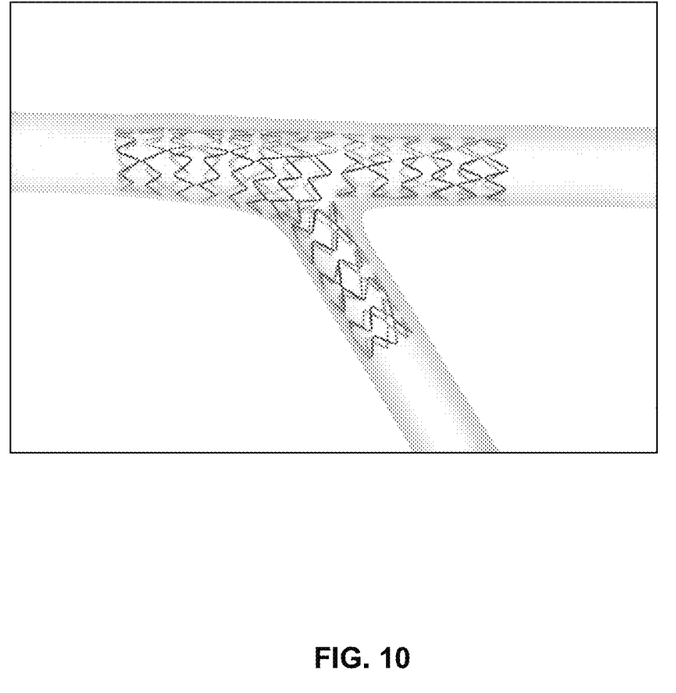
FIG. 10 is a diagram of an example stent placed at a first branch and a second branch of a blood vessel bifurcation.

Quantitative OCT analysis was performed on six equidistant in-stent tissue slices for each stent. Thus a total of 108 [i.e. 6 (animals)*3 (arteries each)*6 (tissue slices)] in-stent tissue slices (cross-sections) were analyzed. The parameters for quantitative analysis included: a) Lumen Area, b) Stent Area, c) Neointimal Area and d) Percent Neointimal Obstruction. FIG. 5 illustrates a table of values of mean and standard derivations of the Average Luminal Areas, Average Stent Areas, Average Neointimal Areas and Average Percent Neointimal Obstruction findings for each group i.e. Control, Sirolimus and Paclitaxel. FIG. 6 illustrates a table of values of mean and standard derivations of the Median Luminal Areas, Median Stent Areas, Median Neointimal Areas and Median Percent Neointimal Obstruction findings for each group. FIG. 7 illustrates a table of values of mean and standard derivations of the Minimal Luminal Areas, Minimal Stent Areas, Minimal Neointimal Areas and Minimal Percent Neointimal Obstruction findings for each group. FIG. 8 illustrates a table of values of mean and standard derivations of the Maximal Luminal Areas, Maximal Stent Areas, Maximal Neointimal Areas and Maximal Percent Neointimal Obstruction findings for each group. It was concluded that out of a data set of the 927 stent struts, just one strut (Paclitaxel) was found to be unequivocally uncovered by the tissues. Based on observation of thrombus it was concluded that drug dose of paclitaxel might be higher than required. The higher dose and vis-a-vis the thrombus effect of the paclitaxel may be attributed to higher in-tissue drug penetration of paclitaxel. Thus the amount of sirolimus of paclitaxel to be coated on the coated balloon is lesser than the amount of sirolimus of paclitaxel loaded on current DEBs.

Various embodiments of the invention provide a drug-delivering balloon that can efficiently deliver the drug to the target site in the blood vessel within a short period for which the drug-delivering balloon comes in contact with the target site. In addition, the invention provides a drug-delivering balloon that can efficiently deliver drug to the maximum area of a lesion and provide for enhance bioavailability with an optimum amount of the drug loaded on the drug-delivering balloon.

Those skilled in the art will realize that the above-recognized advantages and other advantages described herein are merely exemplary and are not meant to be a complete rendering of all of the advantages of the various embodiments of the invention.

In the foregoing specification, specific embodiments of the invention have been described. However, one of ordinary skill in the art appreciates that various modifications and changes can be made to the invention without deviating from the scope of the invention. Accordingly, the specification is to be regarded in an illustrative rather than a restrictive sense, and all such modifications are intended to be included within the scope of the invention.

The invention claimed is:

1. A drug delivery system for delivering at least one drug to at least one of a first branch and a second branch of a blood vessel bifurcation, the drug delivery system comprising:
   a first balloon catheter assembly having a first balloon capable of passing through the blood vessel and being at least partially positioned in the first branch;
   a second balloon catheter assembly having a second balloon capable of passing through the blood vessel and being at least partially positioned in the second branch;
   a hydrophilic surface on at least one of the first balloon and the second balloon; and
   a coating of nano-carriers on the hydrophilic surface, the nano-carriers comprising at least one drug encapsulated with at least one biological agent, the at least one of the first balloon and the second balloon capable of delivering the nano-carriers to at least one of the first branch and the second branch upon being positioned and inflated in the at least one of the first branch and the second branch.

2. The drug delivery system of claim 1, wherein when inflating the at least one of the first balloon and the second balloon at a target site in the at least one of the first branch and the second branch respectively, the nano-carriers are released from the hydrophilic surface within a predetermined duration.

3. The drug delivery system of claim 1, wherein the first balloon catheter assembly and the second balloon catheter assembly comprise a main branch and a side branch.

4. The drug delivery system of claim 3, wherein for treating a bifurcation lesion, at least a main branch balloon is coated with the nano-carriers for drug delivery, and a side branch balloon is uncoated.

5. The drug delivery system of claim 3, wherein for treating a bifurcation lesion, at least a main branch balloon is uncoated, and a side branch balloon is coated with the nano-carriers for drug delivery.

6. The drug delivery system of claim 1, wherein the first balloon catheter assembly is introduced first into a main branch of a blood vessel bifurcation to treat at least the main branch and at least one of the main branch and side branch balloon catheter assemblies has no balloon.

7. A drug delivery system for delivering at least one drug to at least one of a first branch and a second branch of a blood vessel bifurcation, the drug delivery system comprising:
   a first balloon catheter assembly having a first balloon capable of passing through the blood vessel and being at least partially positioned in the first branch;
   a second balloon catheter assembly having a second balloon capable of passing through the blood vessel and being at least partially positioned in the second branch;
   a hydrophilic surface on at least one of the first balloon and the second balloon;
   a coating of nano-carriers on the hydrophilic surface, the nano-carriers comprising at least one drug encapsulated with at least one biological agent, the at least one of the first balloon and the second balloon capable of delivering the nano-carriers to at least one of the first branch and the second branch upon being positioned and inflated in the at least one of the first branch and the second branch;
   a plurality of pores in the coating of the nano-carriers exposing the hydrophilic surface; and
   at least one stent.

8. The drug delivery system of claim 7, wherein the at least one stent is coated with the nano-carriers.

9. The drug delivery system of claim 7, wherein the first balloon and the second balloon comprise a main branch balloon and a side branch balloon; and
   wherein each of the main branch balloon and the side branch balloon have a stent mounted.

10. The drug delivery system of claim 9, wherein each stent is coated with the nano-carriers.

11. The drug delivery system of claim 7, wherein the first balloon and the second balloon comprise a main branch balloon and a side branch balloon; and
   wherein the at least one stent is mounted on a side branch balloon catheter and a main branch balloon catheter is coated with the nano-carriers.

12. The drug delivery system of claim 7, wherein the first balloon and the second balloon comprise a main branch balloon and a side branch balloon; and
   wherein the at least one stent is mounted on a main branch balloon catheter and a side branch balloon catheter is coated with the nano-carriers.

* * * * *